United States Patent [19]

Hahn et al.

[11] 4,142,960
[45] Mar. 6, 1979

[54] SLAB GEL MOLD AND ELECTROPHORESIS APPARATUS

[76] Inventors: Terrance Hahn, 18 Arlington St., Reading, Mass. 01867; Allan M. Maxam, 3½ Wendell St., Cambridge, Mass. 02138

[21] Appl. No.: 829,802

[22] Filed: Sep. 1, 1977

[51] Int. Cl.² ............... G01N 27/26; G01N 27/28
[52] U.S. Cl. ............... 204/299 R; 204/180 G; 23/230 B; 424/12
[58] Field of Search ............... 204/180 G, 299; 23/230 B; 424/12

[56] References Cited

U.S. PATENT DOCUMENTS

| Re. 24,752 | 12/1959 | Ressler | 204/180 G |
| 3,879,280 | 4/1975 | Peterson et al. | 204/180 G X |
| 3,901,782 | 8/1975 | Vadasz et al. | 204/180 G |
| 4,035,377 | 7/1977 | Detroy | 204/299 R |
| 4,049,534 | 9/1977 | Posner | 204/180 G X |

*Primary Examiner*—Arthur C. Prescott
*Attorney, Agent, or Firm*—Richard L. Stevens

[57] ABSTRACT

A vertical slab gel electrophoresis apparatus which has first and second upper electrolytic chambers and a lower electrolytic chamber. A mold assembly containing the slab gel is received in the lower electrolytic chamber and the upper portion of the mold assembly comprises the second upper electrolytic chamber. The first upper electrolytic chamber is spaced apart from the second upper electrolytic chamber. A wick-like material is placed in both the upper electrolytic chambers to provide for electrical communication therebetween.

12 Claims, 4 Drawing Figures

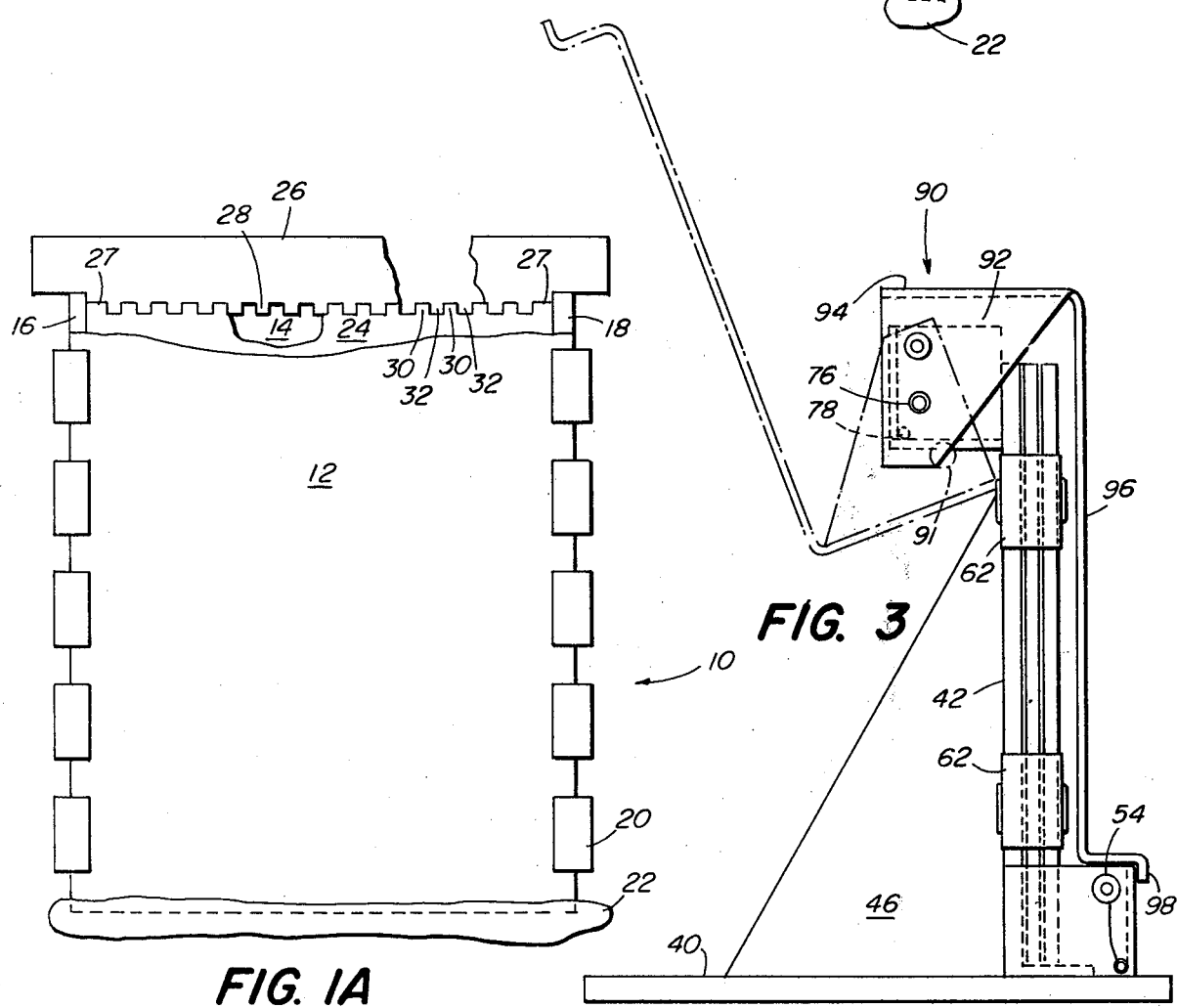
FIG. 1A
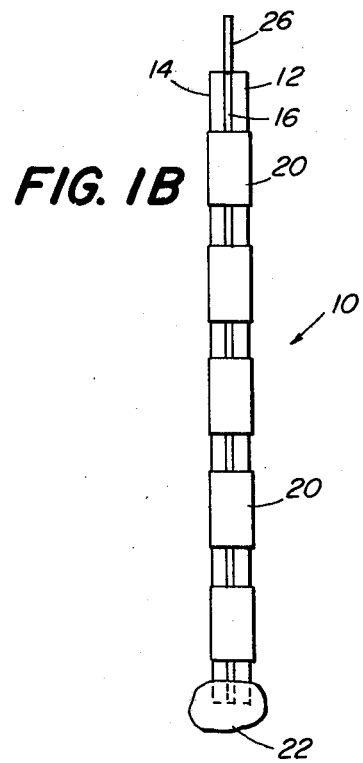
FIG. 1B
FIG. 3

SLAB GEL MOLD AND ELECTROPHORESIS APPARATUS

BACKGROUND OF THE INVENTION

Electrophoresis, generally, relates to the separation of a complex substance into its component fractions by procedures based upon the migration or mobility of electrically charged fractions in a direct current electric field. With an electric field developed between two spaced electrodes and a substance placed therein, the variously charged components or constituents of the substance move or migrate toward the respective electrodes of opposite charge and the respective components or constituents will move with different mobilities, i.e., at different rates. Thus separation may be accomplished on the various component factions. This separation may take place on a suitable support medium such as an acrylamide gel saturated with an electrolyte. Each component separated by the electrophoresis procedure is subject to a qualitative and quantitative analysis and has therefore provided a useful tool in laboratory analysis of various substances such as albumen, enzymes, hemoglobin, carbohydrates, blood serum proteins, nucleic acids, etc.

Vertical gel electrophoresis refers to electrophoresis wherein the component fractions migrate under the influence of an electric field on a gel and in a vertical direction.

In the separation of short segments of DNA and RNA for the purpose of determining their nucleotide sequence, because the gel itself has pores of a specified size, these segments will be drawn through the pores at different speeds depending upon their size — larger ones moving slower than smaller ones. This causes the segments to separate by size or length, which is the desired result both for sequencing and separation.

U.S. Pat. Nos. 3,932,265; 3,980,540; and 3,290,240 are generally representative of the available prior art for vertical gel electrophoresis apparatus.

Typically in commercially available units a comb is inserted into the gel prior to setting. When the gel sets the comb is removed forming slots into which samples are injected. The formation of the gel and slots is generally accomplished after the entire apparatus has been assembled.

A buffer or electrolyte chamber is typically disposed above the slots at the upper portion of the apparatus to insure fluid communication between the chamber and the samples. This arrangement sometimes requires additional structure to achieve cooling; see for example U.S. Pat. No. 3,616,457.

An important drawback in vertical gel electrophoresis is the apparatus typically comprises glass plates which form the walls of a mold into which the gel is placed. These plates have extending outer tabs at the top portion thereof. The upper electrolyte chamber is assembled about these tabs and secured with clamps and gaskets. Further, in some models actual introduction of the gel is accomplished in situ, that is after the entire apparatus has been assembled but prior to the introduction of the electrolyte.

Further gasketing material is used in the region where the tabs of the conventional plates extend into the buffer chamber to prevent leaking and also about the perimeter of the plates.

In setting up the vertical slab gel electrophoresis apparatus it has been found difficult to train personnel adept enough to quickly and efficiently assemble the units. The major problem is in the breaking off of the tabs of the plates in assembling a unit and the time required in properly assembling the unit with the attendant gaskets to prevent leaking.

The present invention overcomes the prior art problems by eliminating the need for tabbed plates used in the mold assembly, and physically separating the upper electrolyte chamber from the sample wells, eliminating the need for gaskets.

SUMMARY OF THE INVENTION

The present invention comprises a vertical slab gel electrophoresis apparatus and method of using the same.

The apparatus generally comprises first and second upper electrolytic chambers and means to provide liquid and electrical communication therebetween, a lower electrolytic chamber and means to establish a potential across the chambers. A mold assembly, containing the gel and the second chamber, is formed externally and subsequently received in the lower chamber and secured in position.

The mold assembly comprises plates held in spaced-apart parallel relationship by spacers disposed between the sides of the plates, the plates and spacers defining the dimensions of the mold cavity. The upper edges of the plates and spacers preferably all lie in the same plane. After a gel has been poured into the cavity a comb is inserted to form the slots for the samples.

In a preferred embodiment of the invention an apertured vertical support plate is provided which supports the mold assembly and forms part of the first upper and the lower electrolytic chambers.

In the preferred embodiment of the invention a wick-like material is disposed in the first and second upper electrolytic chambers to provide for the electrical communication therebetween.

The method of my invention generally includes introducing a gel into a mold assembly, the assembly having upper edges, forming a plurality of projections in the upper surface of the gel, the projections defining slots therebetween, the surfaces of the projections recessed below the upper edges of the mold, and defining with the inner surface of the mold a second electrolytic chamber; placing the mold assembly in a lower electrolytic chamber; establishing a fluid and electrical communication between a first upper electrolytic chamber and the second upper electrolytic chamber, the first upper electrolytic chamber spaced apart from the second upper electrolytic chamber; and applying a potential across the three electrolytic chambers and through the gel whereby samples of charged molecules placed in the slots are separated electrophoretically in the gel slab.

BRIEF DESCRIPTION OF THE DRAWINGS

FIGS. 1A and 1B are front, partly broken away, and side elevations of a mold assembly embodying the present invention;

FIG. 3 is a perspective illustration partly broken away of the apparatus of FIGS. 1 and 2.

DESCRIPTION OF THE PREFERRED EMBODIMENT

Figure 2:
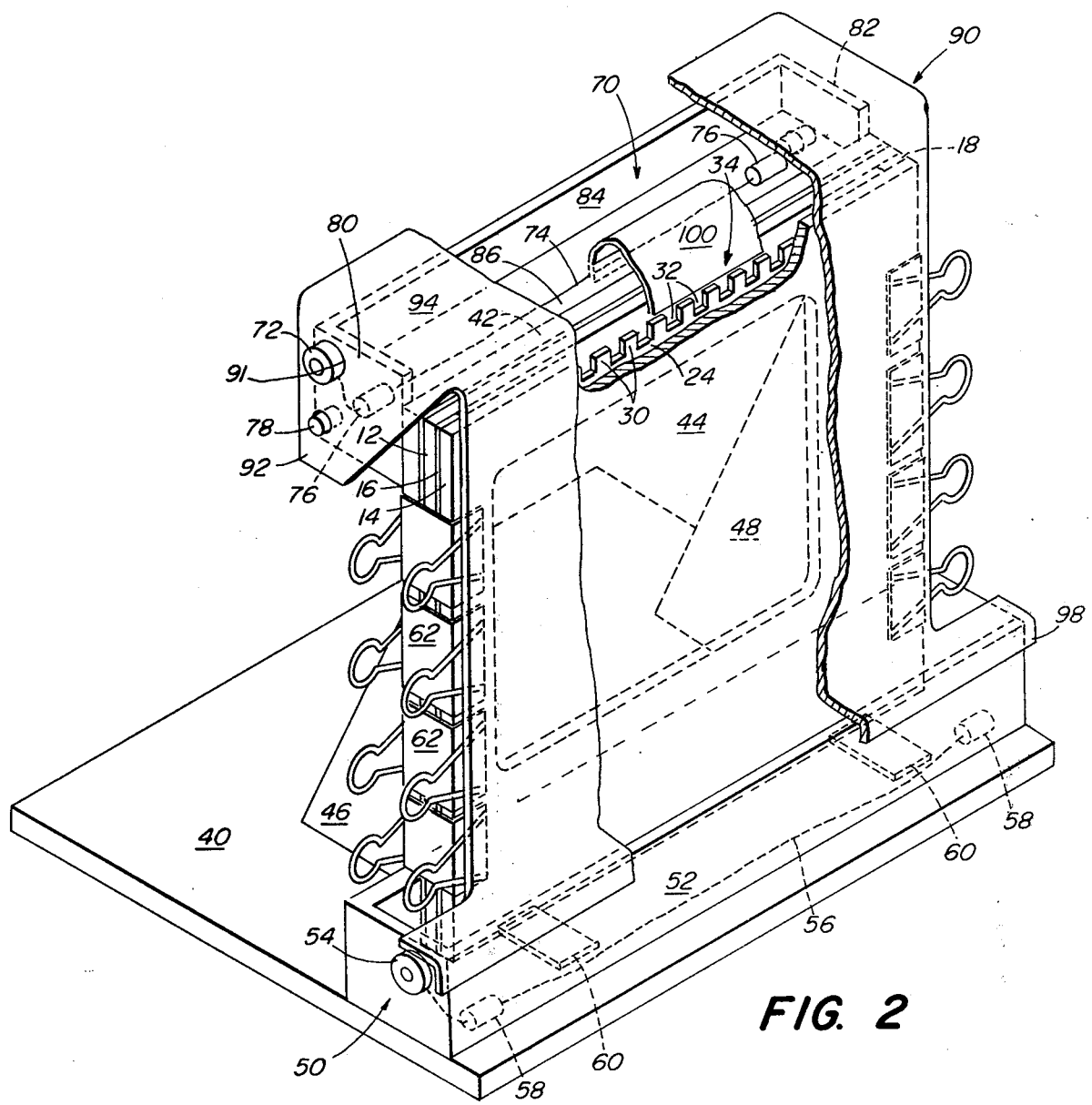
FIG. 2 is a side elevation partially in section of an electrophoresis apparatus embodying the invention.

Referring to FIGS. 1A and 1B a mold assembly 10 comprises generally rectangular glass plates 12 and 14 separated by spacers 16 and 18 all fabricated from an acetal resin such as DELRIN ™. The plates and spacers are secured by clips 20. The upper edges of the plates 12 and 14 and the spacers 16 and 18 all lie in the same plane.

The mold assembly is first set up in this sandwich arrangement. The assembly 10 is then sealed at the bottom with a seal 22 such as soft clay, and filled with a gel solution 24 of acrylamide or agarose and electrolyte. A comb 26 having teeth 28 extending therefrom is inserted into the top of the assembly, the teeth 28 extending into the gel solution 24.

Within minutes the acrylamide polymerizes (or the agarose solidifies) to form a solid gel. Subsequent to the formation of the gel the seal 22 at the bottom is removed and the comb 26 is extracted.

The teeth 28 of the comb 26 form projections 30 in the gel which projections 30 define slots 32 into which the samples to be analyzed are eventually injected. The comb 26 includes depending steps 27 which extend below the upper edge of the mold assembly 10 and are adjacent the inner surfaces of the glass plates 12 and 14 and spacers 16 and 18. As shown more clearly in FIG. 3 when the comb 26 is removed from the mold assembly the upper surfaces of the projections 30 of the gel are below the upper edge of the mold assembly 10. The inner surfaces of the plates 12 and 14 and spacers 16 and 18 and the surface of the projections (after the slots 32 have been filled with samples) define a second upper electrolytic chamber 34.

The mold assembly 10 containing the gel is transferred to the vertical electrophoresis apparatus shown in FIGS. 2 and 3.

The electrophoresis apparatus generally comprises a base plate 40 to which is secured a lower electrolytic chamber 50. A vertical wall 42 has an aperture 44 therein for the cooling of the gel, and triangular braces 46 and 48 are secured to the base plate and the vertical wall.

The lower electrolytic chamber 50 comprises a substantially U-shaped wall 52 sealingly secured both to the upper surface of the base plate 40 and the vertical wall 42, to define the lower chamber 50. A banana plug receptacle 54 is secured to the wall 52 and a platinum wire 56 is secured to the receptacle 54 and positioned in the chamber 50 by wire guides 58. Support blocks 60 are disposed in the bottom of the chamber 50 and the bottom portion of the mold assembly 10 rests on the support blocks 60.

Clips 62 secure the mold assembly 10 to the vertical wall 42. The clips 62 cover the clips 20 shown in FIG. 1. This results in the plate 12 of the assembly 10 being spaced apart from the vertical wall 42 by the thickness of one side of the clip 20, facilitating air circulation. The second upper electrolytic chamber 34, after the assembly 10 has been secured, is adjacent and spaced apart from a first electrolytic chamber 70. Between the chambers 34 and 70 is the upper portion of the glass plate 12 and the vertical wall 42. A paper wick 100 such as a thick, absorbent cellulose paper of coarse fibers bridges the glass plate 12 and vertical wall 42 and provides liquid and electrical communication between the chambers 34 and 70.

The chamber 70 is formed by side walls 80 and 82, a back wall 84 and a floor 86. The front edges of the walls 80 and 82 and the floor 86 are sealingly secured to the vertical wall 42. A banana plug receptacle 72 is secured to the wall 80 and a platinum wire 74 is secured to the receptacle 72 and positioned in the chamber 70 by wire guides 76.

In FIGS. 2 and 3 a cover 90 is shown in the closed position. The cover is shown in its open position in dotted lines in FIG. 3. Referring to FIG. 2 the cover 90 includes sides 92 pivotally secured to the pins 78 which sides 92 depend perpendicularly from a top portion 94. A vertical plate 96 extends downwardly from the top portion 94 turns at its lower end across the lower chamber 50 and terminates as a downwardly extending lip 98. An aperture 91 in the side 92 adjacent chamber side 82 registers with the receptacle 72 when the cover 90 is in its closed position. When the cover 90 is open the side 92 denies access to the receptacle, thereby preventing operation of the apparatus when the cover is in its open position.

In the operation of my invention the mold assembly is formed as shown in FIG. 1. The plates 12 and 14 and spacers 16 and 18 are assembled and secured by clips 20. The spacers 16 and 18 determine the thickness of the gel. A seal 22 is placed at the bottom of the mold 10 and the mold cavity filled with a gel solution and the comb 26 is inserted. For example, if sequencing DNA segments, the procedure as outlined in *PROC. NATL. ACAD. SCI. USA.* 74 PP560–564, Maxam et al., 1977 may be followed.

After the gel has set the seal 22 and comb 26 are removed and the mold assembly 10 is placed in the chamber 50 on supports 60. The assembly 10 is secured to the vertical wall 42 by the clips 62. The samples to be separated electrophoretically in the gel slab 26 are injected into the slots 32 after electrolyte has been placed in the chambers 34, 50 and 70. It is to be understood that in describing the chamber 34 it is possible that the slots may not be entirely filled with sample and accordingly the chamber 34 as defined herein also includes any portion of a slot which is not filled with sample. The current flows from a power source (not shown) through the receptacle 72, the electrode 74, electrolyte in the chamber 70, the paper wick 100, electrolyte in the chamber 34, the slots 32, the gel 26, electrolyte in the chamber 50, the electrode 56, the receptacle 54, and then back to the power source.

The apparatus and method of my invention are particularly suited to the separation of DNA and RNA segments. More particularly by varying the composition of the gel, including acrylamide or agarose density, pH of the electrolyte, and presence or absence of denaturants, DNA or RNA polynucleotides can be separated according to their size, charge or shape.

These techniques are widely known, published aspects of gel electrophoresis. Provision is made for a large enough gel surface area at the bottoms of the slots 32 to accommodate analytic and preparative amounts of DNA and RNA without overloading the gel. The apparatus is designed to operate with higher-than-usual voltages (1000V on the larger model) and a longer-than-usual electrophoretic path (40 cm. from top to bottom of gel on the larger model) — both of which provide better resolution of various DNA and RNA species.

Having described my invention what I now claim is:
1. An electrophoresis apparatus which comprises:
a first integral upper electrolytic chamber;

a lower electrolytic chamber;

a vertical wall secured to the chambers to maintain the chambers in spaced apart relationship;

a mold assembly comprising first and second plates in spaced apart relationship defining a mold cavity therebetween, the cavity adapted to receive a gel, the lower end of the mold assembly disposed in the lower electrolyte chamber, the gel when disposed in the cavity in electrical communication with the electrolyte in the chamber, and the gel when disposed in the cavity forming at the upper end of the mold assembly a plurality of projections, the projections defining a plurality of slots into which samples to be separated electrophoretically may be placed, the upper edges of the projections recessed below the upper edge of the mold assembly, the inner surfaces of the upper end of the mold assembly defining a second integral upper electrolytic chamber, the mold assembly secured to the vertical wall such that the first and second chambers are spatially separated in non-sealing relationship said second chamber being spaced apart and distinct from the first chamber;

means to provide both electrical communication; and liquid-to-liquid communication between electrolyte disposed in the first and second upper electrolytic chambers; and means to generate a current in the chambers whereby a sample introduced into the slots defined by the projections can be electrophoretically separated.

2. The apparatus of claim 1 wherein the means to provide the electrical and liquid communication comprises a wick-like material.

3. The apparatus of claim 2 wherein said material is a paper wick.

4. The apparatus of claim 1 wherein the mold assembly comprises two plates in spaced apart parallel relationship, two spacers disposed between the plates to maintain the plates in parallel relationship and to define the thickness of the gel, the upper edges of the spacers and the upper edges of the glass plates lying in the same plane.

5. The apparatus of claim 4 wherein the mold assembly includes a comb having a plurality of teeth, the comb adapted to be received in the mold cavity, the comb further including steps at either end thereof, said steps adapted to be received in the mold cavity adjacent the spacers.

6. The apparatus of claim 1 which includes a base, the vertical wall secured to the base, and means to secure the mold assembly to the vertical wall.

7. The apparatus of claim 6 wherein the vertical wall includes at least one aperture.

8. The apparatus of claim 6 wherein the vertical wall forms one wall of the lower electrolytic chamber and one wall of the first upper electrolytic chamber;

and the mold assembly includes two plates in spaced apart parallel relationship, two spacers disposed between the plates to maintain the plates in the spaced apart relationship, the second upper electrolytic chamber separated from the first upper electrolytic chamber by the vertical wall which forms a portion of the upper electrolytic chamber and one of said plates.

9. The apparatus of claim 8 which includes first clips to secure the mold assembly and second clips to secure the mold assembly to the vertical wall, the second clips adapted to engage the first clips and the vertical wall whereby the plate of the mold assembly adjacent to the vertical wall is maintained in spaced apart parallel relationship from the vertical wall.

10. The apparatus of claim 9 wherein the means to provide the fluid in electrical communication between the first and second upper electrolytic chambers comprises a paper wick.

11. The apparatus of claim 8 which includes a cover assembly movably secured to the apparatus and operable between a first open position and a second closed position, the cover when in its closed position enclosing all electrolytic chambers; and wherein, the means to generate a current includes a connector secured to one of the chambers, the cover formed to deny access to the connector when in its first open position and to allow access to the connector when in its second closed position.

12. The apparatus of claim 11 wherein the cover assembly includes a side having an aperture therein, the side denying access to the connector when the cover is in its first position and when the cover is in its second position, the aperture is in register with the connector to allow access to the connector.

* * * * *